United States Patent
Mavunkel et al.

(12) 
(10) Patent No.: US 6,448,257 B1
(45) Date of Patent: Sep. 10, 2002

(54) COMPOUNDS AND METHODS TO TREAT CARDIAC FAILURE AND OTHER DISORDERS

(75) Inventors: Babu J. Mavunkel, Sunnyvale; David Y. Liu, Palo Alto; George F. Schreiner, Los Altos Hills; John A. Lewicki, Los Gatos, all of CA (US)

(73) Assignee: Scios, Inc., Sunnyvale, CA (US)

( * ) Notice: Subject to any disclaimer, the term of this patent is extended or adjusted under 35 U.S.C. 154(b) by 0 days.

(21) Appl. No.: 09/535,316

(22) Filed: Mar. 24, 2000

Related U.S. Application Data

(63) Continuation-in-part of application No. 09/316,761, filed on May 21, 1999, which is a continuation-in-part of application No. 09/275,176, filed on Mar. 24, 1999, now Pat. No. 6,340,685, which is a continuation-in-part of application No. 09/128,137, filed on Aug. 3, 1998, now Pat. No. 6,130,235

(60) Provisional application No. 60/086,531, filed on May 22, 1998.

(51) Int. Cl.[7] ..................... A61K 31/437; C07D 471/06
(52) U.S. Cl. ......................................... 514/292; 546/89
(58) Field of Search ............................. 514/292; 546/84

(56) References Cited

U.S. PATENT DOCUMENTS

| | | | |
|---|---|---|---|
| 4,088,765 A | 5/1978 | Winn et al. .................. 514/199 |
| 4,243,806 A | 1/1981 | Raeymaekers et al. ..... 544/396 |
| 4,454,130 A | 6/1984 | Tominago et al. .......... 546/158 |
| 4,600,715 A | * 7/1986 | Huth et al. .................. 514/222 |
| 4,737,501 A | 4/1988 | Tominago et al. .......... 514/253 |
| 4,886,809 A | 12/1989 | Tamada et al. ............. 514/312 |
| 5,462,934 A | 10/1995 | Goto et al. .................. 514/183 |
| 5,698,553 A | 12/1997 | Prucher et al. .......... 514/222.8 |
| 5,714,498 A | 2/1998 | Kulagowski et al. ....... 514/307 |
| 5,726,177 A | 3/1998 | Halazy et al. ............... 514/253 |
| 5,795,907 A | 8/1998 | Kalindjian et al. ......... 514/397 |
| 5,817,871 A | * 10/1998 | Ing et al. ..................... 514/411 |

FOREIGN PATENT DOCUMENTS

| | | |
|---|---|---|
| EP | 0 318 235 | 5/1989 |
| EP | 0 431 945 | 6/1991 |
| EP | 0 709 384 | 5/1996 |
| EP | 0 831 090 | 3/1998 |
| JP | 2-184673 | 7/1990 |
| WO | WO 96/40143 | 12/1996 |
| WO | WO 97/26252 | 7/1997 |
| WO | WO 98/06715 | 2/1998 |
| WO | WO 98/07425 | 2/1998 |
| WO | WO 98/28292 | 7/1998 |
| WO | WO 99/61426 A | 12/1999 |
| WO | WO 00/12074 A | 3/2000 |

OTHER PUBLICATIONS

Adams et al. (1998). CA 128:201066.
De Clerck et al. "Effect of Flunarizine on the Human Red Cell Shape Changes and Calcium Deposition Induced by a 23187," Abstract, *Throm. Res* (1981).23:1–12.

(List continued on next page.)

*Primary Examiner*—Ceila Chang
(74) *Attorney, Agent, or Firm*—Morrison & Foerster LLP

(57) ABSTRACT

Compounds of the formula:

(α)

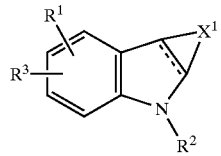

(β)

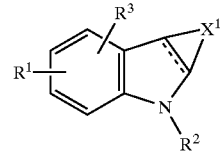

wherein the dotted line represents an optional bond;
and the pharmaceutically acceptable salts thereof,
wherein $X^1$ is an alkyl bridge optionally containing an O, S, or N heteroatom that forms an aliphatic 5–7 membered ring and is optionally substituted by one or more of halo, OR, SR, $NR_2$, RCO, COOR, $CONR_2$, OOCR, or NROCR where R is H or alkyl (1–6C), or by one or more CN or=O, or by one or more aliphatic or aromatic 5- or 6-membered rings optionally containing 1–2 heteroatoms;

$R^1$ is

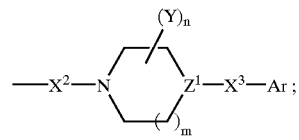

wherein
$X^2$ is CO or an isostere thereof;
m is 0 or 1;
Y is optionally substituted alkyl, optionally substituted aryl, or optionally substituted arylalkyl or two Y taken together may form an alkylene (2–3C) bridge;
n is 0–4;
$Z^1$ is CH or N;
$X^3$ is CH or CHR where R is H or alkyl (1–6C), or an isostere thereof; and
Ar, $R^2$ and $R^3$ are as defined in the specification. These compounds are selective inhibitors of p38α kinase.

17 Claims, No Drawings

OTHER PUBLICATIONS

Dukic et al. (1997). "Synthesis and dopaminergic properties of 3- and 4-substituted 1-{2-[5-(1H-benzimidazole-2thione)]ethyl} piperidines and related compounds," abstract, *Arch Pharm* 330:25–28.

Eyers, P.A. et al. "Conversion of SB 203580-insensitive MAP kinase family members to drug-sensitive forms by a single amino-acid substitution", *Chem and Biol* (1995) 5:321–328.

Fischer, "Physical chemical properties and local anesthetic results of an ether substitute of procaine" CA 67:10051 (1996).

Gassman, P.G., "A General Method for the Synthesis of Indoles," *J Am Chem Soc* (1974) 96(17):5495–5508.

Goehring et al. (2000). CA 132:203174.

Jiang, Y. et al., "Characterization of the structure and function of a new mitogen-activated protein kinase (p38β)" *J Biol Chem* (1996) 271:17920–17926.

Kumar, S. et al. "Novel homologues of CSBP/p38 MAP kinase: activation, substrate specificity and sensitivity to inhibition by pyridinyl imidazoles", *Biochem Biophys Res Comm* (1997) 235:533–538.

Li, Z. et al. "The primary structure of p38γ: a new member of p38 group of MAP kinases", *Biochem Biophys Res Comm* (1996) 228:334–340.

Mittendorf et al. (2000). CA 132:265195.

Murai, Y., et al. "Synthesis of 4-, 5-, 6- and 7-Substituted N-Tosylindoles from Substituted Anilines," *Heterocycles* (1992) 34(5):1017–1029.

Nakai et al. (1994). CA 121:222012.

Nakai et al. (1994). CA 121:221997.

Oelschlaeger et al. (1988). CA 109:73387.

Ogawa et al. (1988). CA 110:57613.

Otsuka Pham. (1983). CA 100:51465.

Otsuka Pharm. (1983). CA 100:34414.

Otsuka Pharm. (1984). CA 100:68187.

Societe des usine chemiques. (1968). CA 77:34584.

Stein, B. et al. "p38-2, a novel mitogen-activated protein kinase with distinct properties", *J Bio Chem* (1997) 272:19509–19517.

Tamada et al. (1989). CA 111:53834.

Von Strandtmann. (1971). CA 80:82713.

Wang, X.S., et al., "molecular cloning and characterization of a novel p38 mitogen-activated protein kinase", *J Biol Chem* (1997) 272:23668–23674.

Wang, Y. et al. "Cardiac Muscle cell hypertrophy and apoptosis induced by distinct members of the p38 mitogen-activated protein kinase family", *J Biol Chem* (1998) 273:2161–2168.

* cited by examiner

COMPOUNDS AND METHODS TO TREAT CARDIAC FAILURE AND OTHER DISORDERS

This applilcation is a cip of Ser. No. 09/316,761 May 21, 1999 which is a cip of Ser. No. 09/275,176 Mar. 24, 1999 now U.S. Pat. No. 6,340,685 which is a cip of Ser. No. 09/128,137 Aug. 3, 1998 now U.S. Pat. No. 6,130,235 which claims benefit of No. 60/086,531 May 22, 1998.

TECHNICAL FIELD

The invention is directed to tricyclic carboxamide compounds that are useful in treating inflammation and that contain a piperazine or piperidine moiety coupled to a phenyl moiety of a tricyclic nucleus. More particularly, the invention concerns novel tricyclic carboxamide compounds having ortho substituted phenyl moieties and N-substituted pyrrole moieties as well as methods to treat heart and kidney conditions using these compounds and derivatives thereof.

BACKGROUND ART

A large number of chronic and acute conditions have been recognized to be associated with perturbation of the inflammatory response. A large number of cytokines participate in this response, including IL-1, IL-6, IL-8 and TNF. It appears that the activity of these cytokines in the regulation of inflammation rely at least in part on the activation of an enzyme on the cell signaling pathway, a member of the MAP kinase family generally known as p38 and alternatively known as CSBP and RK. This kinase is activated by dual phosphorylation after stimulation by physiochemical stress, treatment with lipopolysaccharides or with proinflammatory cytokines such as IL-1 and TNF. Therefore, inhibitors of the kinase activity of p38 are useful antiinflammatory agents.

PCT applications WO98/28292, WO98/06715, WO98/07425, and WO 96/40143, all of which are incorporated herein by reference, describe the relationship of p38 kinase inhibitors with various disease states. As mentioned in these applications, inhibitors of p38 kinase are useful in treating a variety of diseases associated with chronic inflammation. These applications list rheumatoid arthritis, rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis, restenosis, cerebral malaria, chronic pulmonary inflammatory disease, silicosis, pulmonary sarcosis, bone resorption diseases such as osteoporosis, graft-versus-host reaction, Crohn's Disease, ulcerative colitis including inflammatory bowel disease (IBD) and pyresis.

The above-referenced PCT applications disclose compounds which are p38 kinase inhibitors said to be useful in treating these disease states. These compounds are either imidazoles or are indoles substituted at the 3- or 4-position with a piperazine or piperidine ring linked through a carboxamide linkage. Additional compounds which are conjugates of piperazines with indoles are described as insecticides in WO97/26252, also incorporated herein by reference.

DISCLOSURE OF THE INVENTION

The invention is directed to compounds useful in treating inflammation generally, including specific conditions such as those described in the Background section above. Certain novel compounds have been found to inhibit p38 kinase, in particular, p38 kinase α and are thus useful in treating diseases mediated by this enzyme. The compounds of the invention are of the formulas:

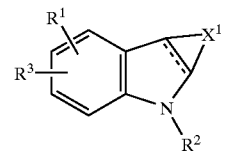

(α)

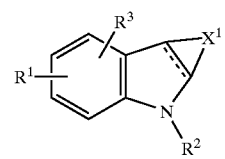

(β)

(wherein the dotted line represents an optional bond) preferably those of the formulas:

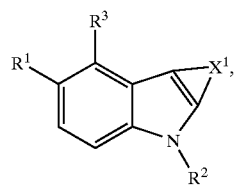

(α')

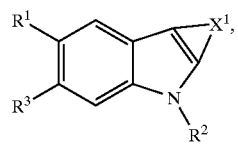

(α'')

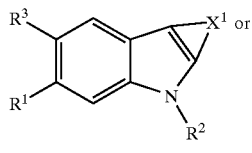

(β')

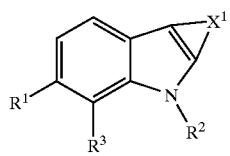

(β'')

and the pharmaceutically acceptable salts thereof,
wherein
$X^1$ is an alkyl bridge optionally containing an O, S, or N heteroatom that forms a fused aliphatic 5–7 membered ring and is optionally substituted by one or more of halo, OR, SR, $NR_2$, RCO, COOR, $CONR_2$, OOCR, or NROCR where R is H or alkyl (1–6C), or by one or more CN or =O, or by one or more aliphatic or aromatic 5- or 6-membered rings optionally containing 1–2 heteroatoms;

$R^1$ is

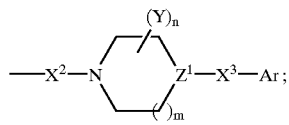

wherein $X^2$ is CO or an isostere thereof;

m is 0 or 1;

Y is optionally substituted alkyl, optionally substituted aryl, or optionally substituted arylalkyl or two Y taken together may form an alkylene (2–3C) bridge;

n is 0–4;

$Z^1$ is CH or N;

$X^3$ is CH or CHR where R is H or alkyl (1–6C), or an isostere thereof; and

Ar consists of one or two phenyl moieties directly coupled to $X^3$ optionally substituted by halo, nitro, alkyl (1–6C), alkenyl (1–6C), alkynyl (1–6C), CN or $CF_3$, or by RCO, COOR, $CONR_2$, $NR_2$, OR, SR, OOCR or NROCR wherein R is H or alkyl (1–6C) or by phenyl, itself optionally substituted by the foregoing substituents;

$R^2$ is H, or is alkyl (1–6C) or aryl each of said alkyl or aryl optionally including one or more heteroatoms which are O, S or N, and optionally substituted by one or more of halo, OR, SR, $NR_2$, RCO, COOR, $CONR_2$, OOCR, or NROCR where R is H or alkyl (1–6C), or by one or more CN or=O, or by one or more aliphatic or aromatic 5- or 6-membered rings optionally containing 1–2 heteroatoms;

$R^3$ is H, halo, $NO_2$, alkyl (1–6C), alkenyl (1–6C), alkynyl (1–6C), CN, OR, SR, $NR_2$, RCO, COOR, $CONR_2$, OOCR, or NROCR where R is H or alkyl (1–6C).

Thus, in one aspect, the invention is directed to compounds of the formulas set forth above. In other aspects, the invention is directed to methods to produce these compounds, to pharmaceutical compositions containing them, and to methods of treating inflammation using these compounds. The invention is also directed to treating conditions associated with cardiac failure using the invention compounds and other compounds described herein.

MODES OF CARRYING OUT THE INVENTION

The compounds of formulas α', α", β' and β" are useful in a variety of physiological contexts, as further described below. Preferred embodiments include those wherein $X^1$ is a heteroalkyl bridge optionally containing an O, S, or N that forms a fused 6-membered aliphatic ring; thus, among the preferred compounds of the invention are derivatives of carboline.

In general, substituents on the nitrogen-containing portion of the pyrrole moiety of the tricyclic ring structure are designed to enhance solubility. Thus, typically, the substituent $R^2$ is polar or contains polar groups.

In other preferred embodiments, the substituents shown for the compounds of the invention are as set forth below.

In regard to $R^1$:

$X^2$ is CO or an isostere thereof. Thus, in addition to CO, $X^2$ may be $CH_2$, SO, $SO_2$, or CHOH. CO is preferred.

$Z^1$ is CH or N; Z=CH is preferred.

Typically m is 1; however, in some compounds of the invention, m can be 0; thus, this substituent can be a five-membered ring.

$X^3$ is CH or CHR where R is H or alkyl (1–6C), or may be an isostere thereof. $X^3$ can be $CH_2$ if Ar consists of a single phenyl moiety or CH if Ar consists of two phenyl moieties. Thus, for appropriate embodiments of Ar, $X^3$ may be any of the alternatives set forth above for $X^2$.

The phenyl moieties represented by Ar may optionally be substituted by substituents including alkyl (1–6C), halo, RCO, COOR, $CONR_2$, OR, SR, $NR_2$, OOCR, NROCR, $NO_2$, CN, or $CF_3$, wherein R is H or alkyl (1–6C). The phenyl moieties may also be substituted with an additional phenyl residue, preferably at the 4-position. The additional phenyl residue may itself be substituted with the substituents set forth above. The additional phenyl may be substituted in all five positions, but preferably less, preferably in 1–2 positions or not at all. Preferred substituents include alkyl (1–6C), OR, $NR_2$ and halo, especially halo and $OCH_3$. The substituents may occupy all five positions of the phenyl substituent, preferably 1–2 positions or the phenyl may be unsubstituted.

n may be 0–4, and is preferably 0. However, when n is 1, Y is present and may be alkyl, arylalkyl or aryl, all of which may optionally be substituted by the substituents set forth above with regard to Ar. When n is 2, both Y groups together may constitute an alkylene bridge. A preferred bridge is an ethylene bridge. Preferred embodiments of Y when n is 1 include unsubstituted alkyl and unsubstituted arylalkyl.

With regard to $R^2$:

$R^2$ is preferably H, but may also be a suitable substituent. Such substituents are typically and preferably alkyl or substituted alkyl, —COR, —COOR, $CONR_2$, $SO_2NR_2$, OR, SR, $NR_2$, $NO_2$, CN and $CF_3$ where R is H or alkyl (1–6C). The alkyl or substituted alkyl may optionally include one or more heteroatoms which can be O, N or S, preferably N and O. Permitted substitutions on the alkyl group are set forth above; preferred substituents include OR, where R is H or alkyl (1–6C) and=O. Also included among the preferred substituents on the alkyl group are cyclic moieties, such as piperazine, pyridine, piperidine, phenyl, and the like. Preferably, the alkyl embodiments of $R^2$ contain 0, 1 or 2 substituents. Among preferred embodiments of $R^2$ are included those of the formula —(CO)O—Y' wherein Y' is, for example, —$(CH_2)_n NR_2$, where n is an integer of 0–6 and R is as defined above.

With respect to $R^3$:

$R^3$ is preferably H, but may also be a suitable substituent. Such substituents include halo, OR, $NR_2$, and alkyl (1–6C). OR is preferred and methoxy is particularly desirable.

Preferred embodiments of $X^1$ include those of the formula —$(CH_2)_p N(CH_2)_q$— wherein p or q are integers of 0–4.

More preferable embodiments of $X^1$ include those of the formulas —$CH_2N(CH_2)_2$— and —$(CH_2)_2NCH_2$—.

The compounds of formulas α', α", β' and β" may be supplied in the form of their pharmaceutically acceptable acid-addition salts including salts of inorganic acids such as hydrochloric, sulfuric, hydrobromic, or phosphoric acid or salts of organic acids such as acetic, tartaric, succinic, benzoic, salicylic, and the like. If a carboxyl moiety is present, these compounds may also be supplied as a salt with a pharmaceutically acceptable base, including inorganic bases such as sodium hydroxide, potassium hydroxide, calcium hydroxide, ammonium hydroxide and the like or a salt with a organic base such as caffeine.

Particularly preferred compounds of the invention are of formulas (A) and (B):

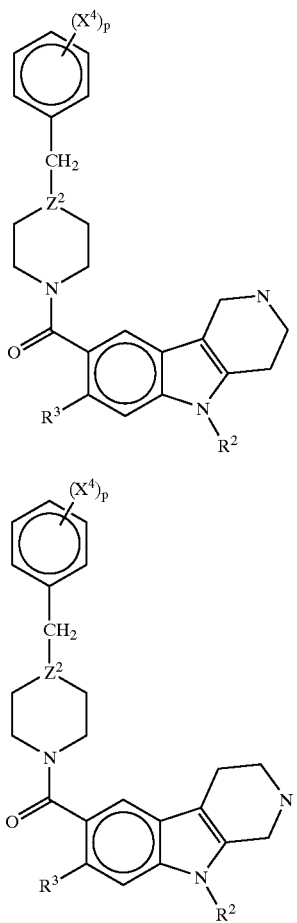

(A)

(B)

In these compounds, $R^1$ is of the formula shown, wherein each $X^4$ is independently halo, preferably fluoroalkyl (1–6C), OR or $NR_2$, wherein R is H or alkyl (1–6C), and p is an integer of 0–3. $R^2$ and $R^3$ are as defined above. $Z^2$ is N or CH.

Also preferred are similar compounds where the positions of $R^3$ and the illustrated embodiment of $R^1$ are reversed; i.e., $R^3$ is at the position where $R^1$ is illustrated and $R^1$ is at the position where $R^3$ is illustrated.

Synthesis of the Invention Compounds

The compounds of the invention can be synthesized by a variety of methods most of them known in the art per se. The tricyclic nucleus may be supplied per se and the substituent $R^1$ coupled thereto. Alternatively, the tricyclic moiety can be synthesized using, for example, an appropriately substituted aminobenzoic acid or amninobenzoate derivative which may then be cyclized and then substituted with $R^1$.

Thus, for example, as shown in Reaction Scheme 1, a piperidine carboxylic acid protected with tert-butyloxycarbonyl (BOC) is coupled to 4-hydrazinobenzoic acid in the presence of an alcohol which is then cyclized in the presence of an acid to form the tetrahydro carboline derivative moiety. The carboline derivative moiety, which is protected with BOC, is coupled to 4-benzyl piperidine in a reaction mixture containing a coupling agent such as EDAC to obtain the coupled carboxamide, and is then deprotected. The double bond between the pyrrole moiety and the 6-membered aliphatic ring can be optionally further reduced by hydrogenation or with a reducing agent such as palladium.

Scheme 1

SYNTHESIS OF γ-CARBOLINES

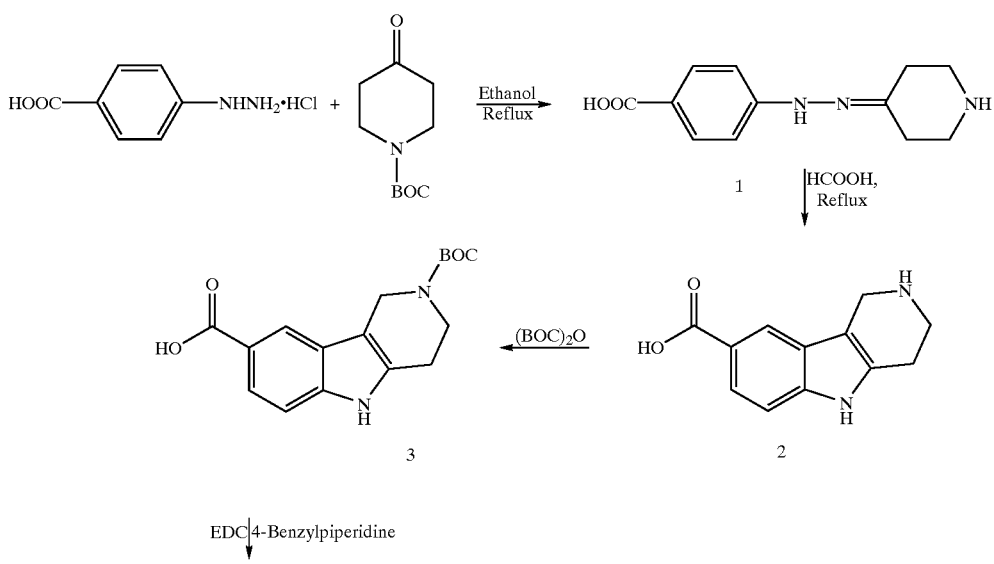

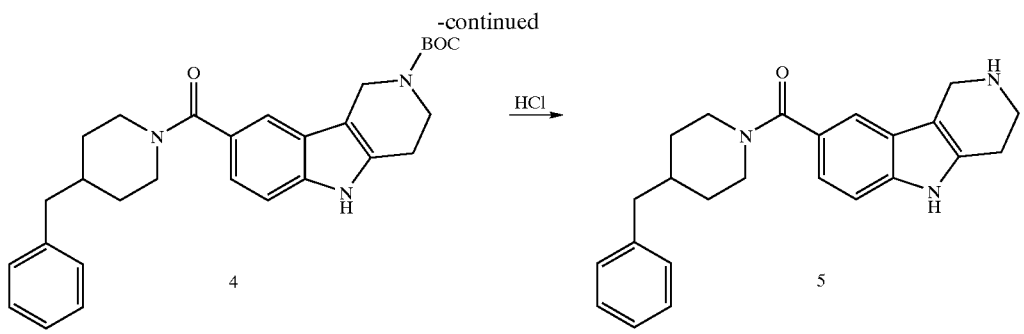

As shown in Reaction Scheme 2, 3-carbethoxy-2-piperidone is coupled to an appropriately substituted aminobenzoate and then cyclized in the presence of an acid to form the tetrahydrocarboline derivative moiety. The carboline moiety can either be coupled (after converting ester to acid) to 4-benzyl pyridine in a reaction mixture containing a coupling agent such as EDAC to obtain a coupled carboxamide containing an amide in the tricyclic moiety, or in a reaction mixture containing a base and a reducing agent such as $BH_3$ to obtain a coupled carboxamide. The double bond between the pyrrole moiety and the 6-membered aliphatic ring can be optionally further reduced by hydrogenation or with a reducing agent such as palladium.

Administration and Use

The compounds of the invention are useful in treating conditions associated with inflammation. Thus, the compounds of formulas (1)–(4) or their pharmaceutically acceptable salts are used in the manufacture of a medicament for prophylactic or therapeutic treatment of mammals, including humans, in respect of conditions characterized by excessive production of cytokines and/or inappropriate or unregulated cytokine activity on such cells as cardiomyocytes, cardiofibroblasts and macrophages.

The compounds of the invention inhibit the production of cytokines such as TNF, IL-1, IL-6 and IL-8, cytokines that are important proinflammatory constituents in many different disease states and syndromes. Thus, inhibition of these

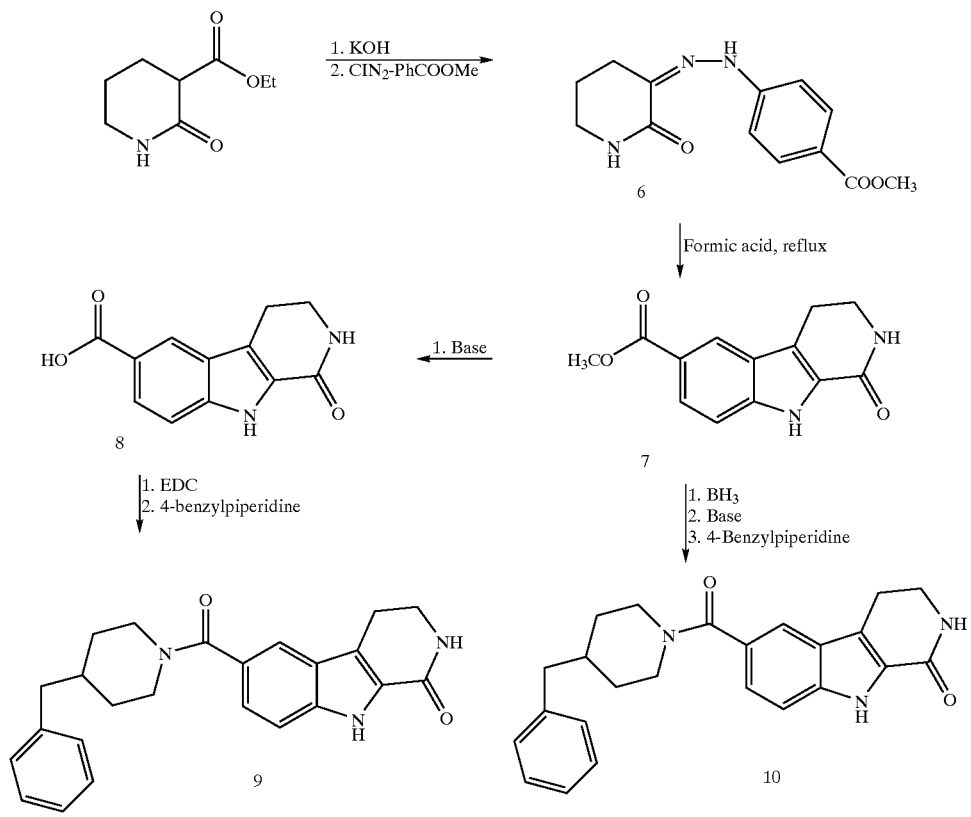

Scheme 2
SYNTHESIS OF β-CARBOLINES cytokines has benefit in controlling and mitigating many diseases. The compounds of the invention inhibit a member of the MAP kinase family variously called p38 MAPK (or p38), CSBP, or SAPK-2. The activation of this protein has been shown to regulate the production of prostanoids, such as PGE2, and matrix metalloproteinases, such as collagenase-3, and to accompany exacerbation of the diseases in response to stress caused, for example, by treatment with lipopolysaccharides or cytokines such as TNF and IL-1. Inhibition of p38 activity, therefore, is predictive of the ability of a medicament to provide a beneficial effect in treating diseases such as coronary artery disease, congestive heart failure, cardiomyopathy, myocarditis, vasculitis, restenosis, such as occurs following coronary angioplasty, atherosclerosis, rheumatoid arthritis, rheumatoid spondylitis, osteoarthritis, gouty arthritis and other arthritic conditions, multiple sclerosis, acute respiratory distress syndrome (ARDS), asthma, chronic obstructive pulmonary disease (COPD), silicosis, pulmonary sarcosis, sepsis, septic shock, endotoxic shock, toxic shock syndrome, heart and brain failure (stroke) that are characterized by ischemia and reperfusion injury, surgical procedures, such as transplantation procedures and graft rejections, cardiopulmonary bypass, coronary artery bypass graft, CNS injuries, including open and closed head trauma, inflammatory eye conditions such as conjunctivitis and uveitis, acute renal failure, glomerulonephritis, inflammatory bowel diseases, such as Crohn's disease or ulcerative colitis, graft vs. host disease, bone resorption diseases like osteoporosis, type II diabetes, pyresis, psoriasis, cachexia, viral diseases such as those caused by HIV, CMV, and Herpes, and cerebral malaria, tumor metastases and acute pain, such as that accompanying dental surgery, dysmenorrhea and post-orthopedic surgery.

Within the last several years, p38 has been shown to comprise a group of MAP kinases designated p38α, p38β, p38γ and p38δ. Jiang, Y. et al. *J Biol Chem* (1996) 271:17920–17926 first reported characterization of p38β as a 372-amino acid protein closely related to p38α. Kumar, S. et al. *Biochem Biophys Res Comm* (1997) 235:533–538 and Stein, B. et al. *J Biol Chem* (1997) 272:19509–19517 reported a second isoform of p38β, p38β2, containing 364 amino acids with 73% identity to p38α. All of these reports show evidence that p38β is activated by proinflammatory cytokines and environmental stress, although the second reported p38β isoform, p38β2, appears to be preferentially expressed in the CNS, heart and skeletal muscle compared to the more ubiquitous tissue expression of p38α. Furthermore, activated transcription factor-2 (ATF-2) was observed to be a better substrate for p38β2 than for p38α, thus suggesting that separate mechanisms of action may be associated with these forms. The physiological role of p38β1 has been called into question by the latter two reports since it cannot be found in human tissue and does not exhibit appreciable kinase activity with the substrates of p38α.

The identification of p38γ was reported by Li, Z. et al. *Biochem Biophys Res Comm* (1996) 228:334–340 and of p38δ by Wang, X., et al., *J Biol Chem* (1997) 272:23668–23674 and by Kumar, S., et al., *Biochem Biophys Res Comm* (1997) 235:533–538. The data suggest that these two p38 isoforms (γ and δ) represent a unique subset of the MAPK family based on their tissue expression patterns, substrate utilization, response to direct and indirect stimuli, and susceptibility to kinase inhibitors.

Various results with regard to response to drugs targeting the p38 family as between p38α and either the putative p38β1 or p38β2 or both were reported by Jiang, Kumar, and Stein cited above as well as by Eyers, P. A. et al. *Chem and Biol* (1995) 5:321–328. An additional paper by Wang, Y. et al. *J Biol Chem* (1998) 273:2161–2168 suggests the significance of such differential effects. As pointed out by Wang, a number of stimuli, such as myocardial infarction, hypertension, valvular diseases, viral myocarditis, and dilated cardiomyopathy lead to an increase in cardiac workload and elevated mechanical stress on cardiomyocytes. These are said to lead to an adaptive hypertrophic response which, if not controlled, has decidedly negative consequences. Wang cites previous studies which have shown that in ischemia reperfusion treated hearts, p38 MAPK activities are elevated in association with hypertrophy and programmed cell death. Wang shows in the cited paper that activation of p38β activity results in hypertrophy, whereas activation of p38α activity leads to myocyte apoptosis. Thus, selective inhibition of p38α activity as compared to p38β activity will be of benefit in treating conditions associated with cardiac failure. These conditions include congestive heart failure, cardiomyopathy, myocarditis, vasculitis, vascular restenosis, valvular disease, conditions associated with cardiopulmonary bypass, coronary artery bypass, grafts and vascular grafts. Further, to the extent that the a-isoform is toxic in other muscle cell types, α-selective inhibitors would be useful for conditions associated with cachexia attributed to TNF or other conditions such as cancer, infection, or autoimmune disease.

The compounds described herein which selectively inhibit the activity of the p38α isoform are useful for treating conditions associated with activation of p38α, in particular those associated with cardiac hypertrophy, ischemia or other environmental stress such as oxidation injury, hyperosmolarity or other agents or factors that activate p38α kinase, or cardiac failure, for example, congestive heart failure, cardiomyopathy and myocarditis.

Compounds which exhibit this activity are of the formula (δ)

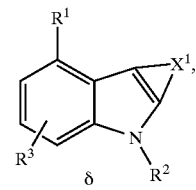

(η)

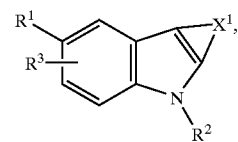

(λ)

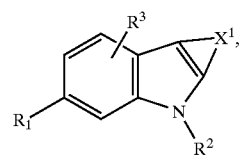

-continued

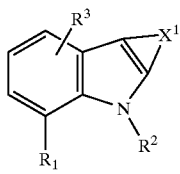

(ε)

wherein $R^1$, $R^2$, $R^3$ and $X^1$ are as defined in claim 1.

The manner of administration and formulation of the compounds described herein will depend on the nature of the condition, the severity of the condition, the particular subject to be treated, and the judgement of the practitioner; formulation will depend on mode of administration. As these compounds are small molecules, they are conveniently administered by oral administration by compounding them with suitable pharmaceutical excipients so as to provide tablets, capsules, syrups, inhaled aerosols and the like. Suitable formulations for oral administration may also include minor components such as buffers, flavoring agents and the like. Typically, the amount of active ingredient in the formulations will be in the range of 5%–95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences*, latest edition, Mack Publishing Company, Easton, Pa. Reference to this manual is routine in the art.

The dosages of the compounds of the invention will depend on a number of factors which will vary from patient to patient. However, it is believed that generally, the daily oral dosage will utilize 0.001–100 mg/kg total body weight, preferably from 0.01–50 mg/kg and more preferably about 0.01 mg/kg–10 mg/kg. The dose regimen will vary, however, depending on the conditions being treated and the judgment of the practitioner.

As implicated above, although the compounds of the invention may be used in humans, they are also available for veterinary use in treating animal subjects.

The following examples are intended to illustrate but not to limit the invention.

Examples 1–3 illustrate Reaction Scheme 1:

EXAMPLE 1

Preparation of γ-carboline carboxylic acid Derivative of Formula 3

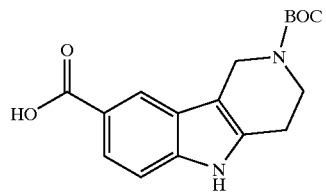

(3)

3.8 g (20 mmol) 4-hydrazinobenzoic acid hydrochloride and 4.0 g (20 mmol) of tert butyl-4-oxo-1-piperidine carboxylic acid was refluxed in 100 mL ethanol for 24 hours. It was concentrated and cooled upon which 3.85 g of the hydrazone of formula (1) in Scheme 1 crystallized out. MS: 233, $M^+$.

3.85 g (16.52 mmol) of the hydrazone of formula (1) was heated at reflux in 60 mL of 85% formic acid for 24 hours. The solvent was removed in vacuo and the residue dissolved in aqueous ethanol and the pH was adjusted to about 9 by the addition of 20% NaOH solution. Di-tert-butyldicarbonate (4.0 g) was added and the mixture stirred at ambient temperature for 24 hours. After removing the ethanol under reduced pressure, the remaining solution was diluted with water and extracted with dichloromethane (3×75 mL). The combined extract was washed with water, dried over $MgSO_4$ and concentrated. The residue was purified by chromatography on silica gel with ethylacetate-hexane (4:6) to yield 650 mg of the desired product of formula (3) above. MS: 316, $M^+$.

EXAMPLE 2

Preparation of Protected benzyl piperidinyl γ-carboline carboxamide Derivative of Formula 4

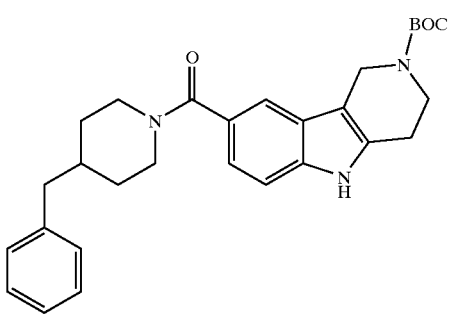

(4)

610 mg (1.93 mmol) of the acid of formula (3) was dissolved in 15 mL dry DMF and reacted with 450 mg (2.25 mmol) of EDC for 20 min. 350 mg (2 mmol) 4-benzylpiperidine was added followed by 20 mg DMAP (catalyst). The mixture was allowed to stir for 20 hours. The reaction mixture was diluted with water and the product was extracted out with dichloromethane (3×75 mL), the combined extracts were washed with brine, and dried. After drying and evaporation of the solvent, the product was purified by chromatography on silica gel with ethylacetate-hexane (4:6) to yield 480 mg of the compound of formula (4) above.

EXAMPLE 3

Preparation of Deprotected piperidinyl-γ-carboline carboxamide Derivative of Formula 5

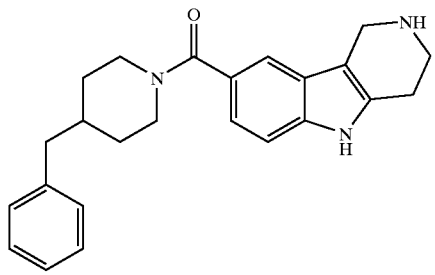

(5)

The compound of formula (4) was converted to the hydrochloride salt of formula (5) above by treating with dioxane-HCl (4 M). MS: 373, M$^+$.

Examples 4–8 illustrate Reaction Scheme 2:

EXAMPLE 4

Preparation of the hydrazone of Formula 6

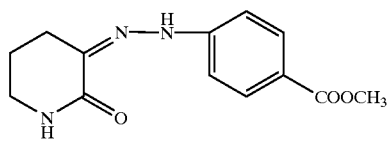

(6)

8.56 g (50 mmol) of 3-carbethoxy-2-piperidone was stirred with 100 mL water containing 3.3 g (85%, 50 mmol) KOH for 48 hours at room temperature. To this was added the diazonium salt of methyl-4-aminobenzoate (7.5 g, 50 mmol) prepared by treating an ice cold solution of methyl-4-aminobenzoate in 9.6 mL concentrated HCl and 40 mL water with sodium nitrite (4.14 g, 60 mmol) in portions over 30 min. with additional stirring for 10 min. at 0° C. The temperature of the reaction mixture was maintained at 0 to −2° C. through the addition. After the addition, 20% aqueous NaOH solution was added to adjust the pH to 5 and the mixture was allowed to stir for 24 hours. The desired product (12 g) was collected by filtration, washed with water and dried. This product of formula (6) above was used without further purification.

EXAMPLE 5

Preparation of the β-carbolinone ester Derivative of Formula 7

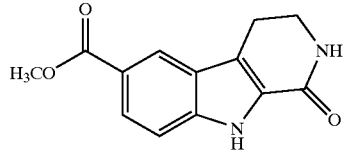

(7)

Hydrazone of formula (6) (12 g, 45.98 mmol) is heated at reflux with 50 mL of 85% formic acid for 2.5 hours. It was cooled and filtered. The solid obtained was washed with water and a small volume of cold ethanol and dried to give the product of formula (7) above (7.3 g). MS: 244, M+.

EXAMPLE 6

Preparation of the β-carbolinone acid Derivative of Formula 8

(8)

1.2 g (4.9 mmol) of the compound of formula (7) was stirred with 10 mL 20% aqueous NaOH solution in 40 mL methanol for 20 hours. 10 mL water was added and the mixture refluxed for 2 hours. After the removal of methanol, the mixture was further diluted with water and acidified with concentrated HCl. The precipitated product of formula (8) above was isolate and dried. Yield: 575 mg., MS: 230, M$^+$.

EXAMPLE 7

Preparation of the β-benzyl piperidinyl carbolinone carboxamide Derivative of Formula 9

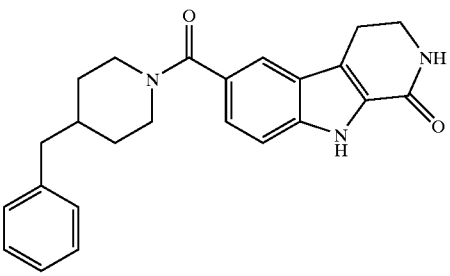

(9)

The carboxamide of formula (9) above was prepared using the procedure described for compound of formula (4). MS: 387, M$^+$.

EXAMPLE 8

Preparation of the β-benzyl piperidinyl carboline carboxamide Derivative of Formula 10

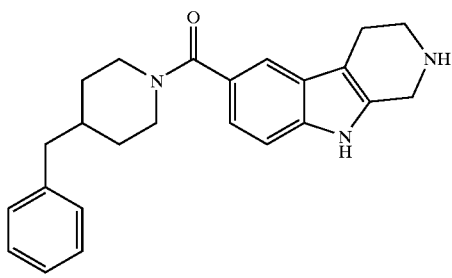

(10)

A. 3.66 g (15 mmol) of the amide of formula (7) was taken in 70 mL THF and refluxed with 35 mmol $BH_3.Me_2S$ (3.5 mL, 10 M solution in THF) for 8 hours. 40 mL methanolic HCl was added and refluxed for 1 hour. The solvents were removed under reduced pressure and the residue was refluxed again with 25 mL methanolic HCl. After evaporation, the salt obtained was dissolved in ethanol-water and the pH is adjusted to 9 by the addition of 20% aqueous NaOH solution. 20 mmol of di-tert butyl dicarbonate was added and the mixture was allowed to stir for 20 hours. After the removal of ethanol, the product was extracted with ethylacetate and purified by silica gel chromatography eluting with ethylacetate-hexane (20 to 40% ethylacetate, gradient) to yield 1.62 g of the product. MS: 330, $M^+$.

990 mg (3 mmol) of the ester obtained from the previous step was taken in 40 mL methanol-water mixture and refluxed with 1 g (25 mmol) NaOH for 2 hours. It was cooled and the methanol was removed in vacuo. The aqueous solution was diluted with water and acidified carefully by the addition of 2 N HCl. The precipitated product was collected by filtration and dried. Yield: 600 mg., MS: 316 $M^+$.

The acid obtained from the previous step was coupled with 4-benzylpiperidine and the deprotection of the amine using dioxane-HCl was carried out as previously reported for the compound of formula (5). MS: 373, $M^+$.

B. Using the procedure of Example 8, the following were prepared:

| Preparation of | Substituting for 4-benzyl piperidine |
|---|---|
| 11 (MS: 374, $M^+$) | 4-benzyl piperazine |
| 12 (MS: 391, $M^+$) | 4-(4-fluorobenzyl) piperazine |

Using the procedure for Examples 4–8, the following were prepared with a modification as discussed below:

| Preparation of | Substituting for methyl-4-aminobenzoate | Substituting for 4-benzyl piperidine |
|---|---|---|
| 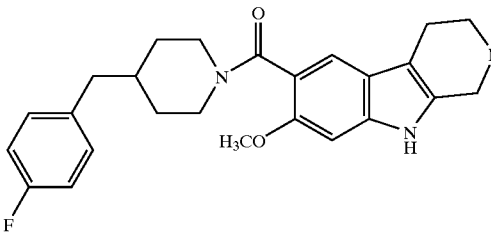<br>13<br>(MS: 422, M⁺) | 4-amino-2-methoxymethyl benzoate | 4-fluorobenzyl piperidine |
| 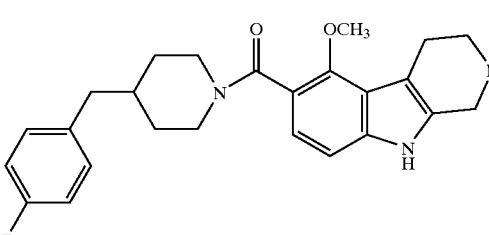<br>14<br>(MS: 422, M⁺) | 4-amino-2-methoxymethyl benzoate | 4-fluorobenzyl piperidine |

After cyclization with formic acid, reduction with $BH_3$ and treatment with di-tert butyl dicarbonate, the two isomers were separated using silica gel chromatography. The two isomers were separately hydrolyzed and coupled with 4-F-benzylpiperidine to obtain the compounds of formulas (13) and (14).

For each of the assay procedures described below, the TNF-α production correlates to the activity of p38-α kinase.

EXAMPLE 9

A. Human Whole Blood Assay for p38 Kinase Inhibition

Venous blood is collected from healthy male volunteers into a heparinized syringe and is used within 2 hours of collection. Test compounds are dissolved in 100% DMSO and 1 μl aliquots of drug concentrations ranging from 0 to 1 mM are dispensed into quadruplicate wells of a 24-well microtiter plate (Nunclon Delta SI, Applied Scientific, So. San Francisco, Calif.). Whole blood is added at a volume of 1 ml/well and the mixture is incubated for 15 minutes with constant shaking (Titer Plate Shaker, Lab-Line Instruments, Inc., Melrose Park, Ill.) at a humidified atmosphere of 5% $CO_2$ at 37° C. Whole blood is cultured either undiluted or at a final dilution of 1:10 with RPMI 1640 (Gibco 31800+ $NaHCO_3$, Life Technologies, Rockville, Md. and Scios, Inc., Sunnyvale, Calif.). At the end of the incubation period, 10 μl of LPS (E. coli 0111:B4, Sigma Chemical Co., St. Louis, Mo.) is added to each well to a final concentration of 1 or 0.1 μg/ml for undiluted or 1:10 diluted whole blood, respectively. The incubation is continued for an additional 2 hours. The reaction is stopped by placing the microtiter plates in an ice bath and plasma or cell-free supernates are collected by centrifugation at 3000 rpm for 10 minutes at 4° C. The plasma samples are stored at −80° C. until assayed for TNF-α levels by ELISA, following the directions supplied by Quantikine Human TNF-α assay kit (R&D Systems, Minneapolis, Minn.).

$IC_{50}$ values are calculated using the concentration of inhibitor that causes a 50% decrease as compared to a control.

B. Enriched Mononuclear Cell Assay for p38 Kinase Inhibition

The enriched mononuclear cell assay, the protocol of which is set forth below, begins with cryopreserved Human Peripheral Blood Mononuclear Cells (HPBMCs) (Clonetics Corp.) that are rinsed and resuspended in a warm mixture of cell growth media. The resuspended cells are then counted and seeded at 1×10⁶ cells/well in a 24-well microtitre plate. The plates are then placed in an incubator for an hour to allow the cells to settle in each well.

After the cells have settled, the media is aspirated and new media containing 100 ng/ml of the cytokine stimulatory factor Lipopolysaccharide (LPS) and a test chemical compound is added to each well of the microtiter plate. Thus, each well contains HPBMCs, LPS and a test chemical compound. The cells are then incubated for 2 hours, and the amount of the cytokine Tumor Necrosis Factor Alpha (TNF-α) is measured using an Enzyme Linked Immunoassay (ELISA). One such ELISA for detecting the levels of TNF-α is commercially available from R&D Systems. The amount of TNF-α production by the HPBMCs in each well is then compared to a control well to determine whether the chemical compound acts as an inhibitor of cytokine production.

LPS Induced Cytokine Synthesis in HPBMCs

Cryopreserved HPBMC (cat#CC-2702 Clonetics Corp)

LGM-3 media (cat#CC-3212 Clonetics Corp)

LPS stock 10 μg/ml (Cat. No. L 2630 serotype 0111:B4 Sigma)

Human TNF-α ELISA (R&D Systems)

DNase I (10 mg/ml stock)

Preparation of Cells

LGM-3 media warmed to 37° C.

5 μl of DNase I stock added to 10 ml media.

Cells thawed rapidly and dispersed into above.

Centrifuge 200×g×10 min @ RT.

Pellet up in 10 ml sterile PBS.

Centrifuge 200×g×10 min @ RT.

Pellet resuspended in 10 ml LGM-3 then diluted to 50 ml with LGM-3.

Perform cell count.

Adjust to 1×E06 cells/well.

Seed 1 ml/well of a 24 well plate.

Place plate in incubator to plate down for 1 hour.

Preparation of Incubation Media

LGM-3 containing 100 ng/ml LPS (e.g. 50 ml media plus 0.5 ml LPS stock)

Aliquot into 2 ml aliquots and add 1000×inhibitor dilutions.

Incubation

When cells have plated down aspirate media away and overlay with 1 ml relevant incubation media. Return plate to incubator for 2 hours or 24 hours. Remove supernatants after incubation to a labeled tube and either perform TNF (or other) ELISA immediately or freeze for later assay.

$IC_{50}$ values are calculated using the concentration of inhibitor that causes a 50% decrease as compared to a control.

EXAMPLE 10

Activity of the Invention Compounds

The inhibition ($IC_{50}$) of p38α by the following inventive compounds is from about 0.01–1 μM.

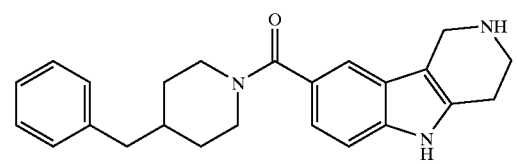

(4-Benzyl-piperidin-1-yl)-(2,3,4,5-tetrahydro-1H-pyrido[4,3-b]indol-8-yl)-methanone

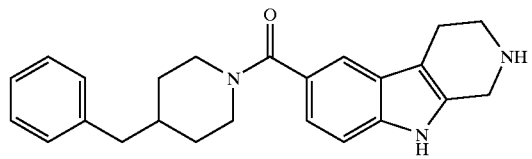

(4-Benzyl-piperidin-1-yl)-(2,3,4,9-tetrahydro-1H-β-carbolin-6-yl)-methanone

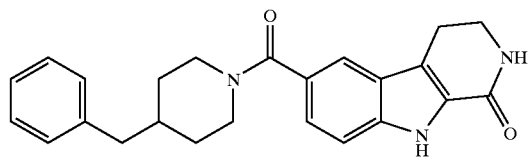

6-(4-Benzyl-piperidine-1-carbonyl)-2,3,4,9-tetrahydro-β-carbolin-1-one

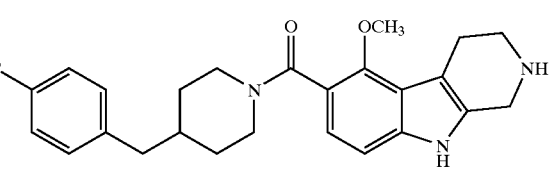

[4-(4-Fluoro-benzyl)-piperidin-1-yl]-(5-methoxy-2,3,4,9-tetrahydro-1H-β-carbolin-6-yl)-methanone

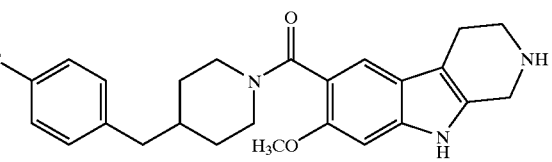

[4-(4-Fluoro-benzyl)-piperdin-1-yl]-(7-methoxy-2,3,4,9-tetrahydro-1H-β-carbolin-6-yl)-methanone

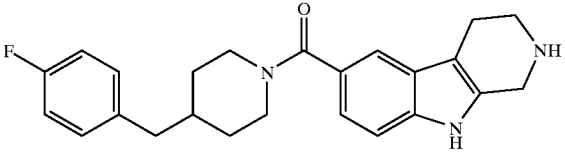

[4-(4-Fluoro-benzyl)-piperidin-1-yl]-(2,3,4,9-tetrahydro-1H-β-carbolin-6-yl)-methanone

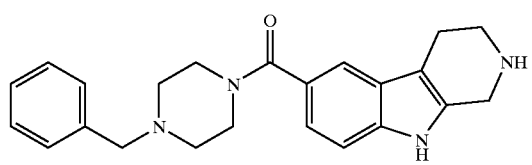

(4-Benzyl-piperazin-1-yl)-(2,3,4,9-tetrahydro-1H-β-carbolin-6-yl)-methanone

What is claimed is:

1. The compound of the formula:

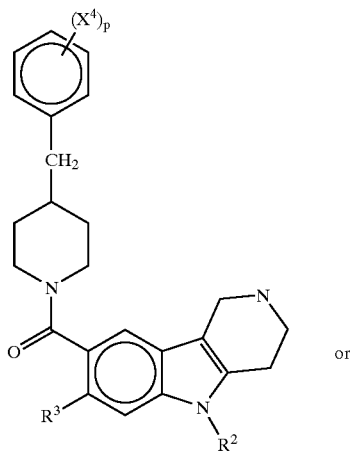
(A)

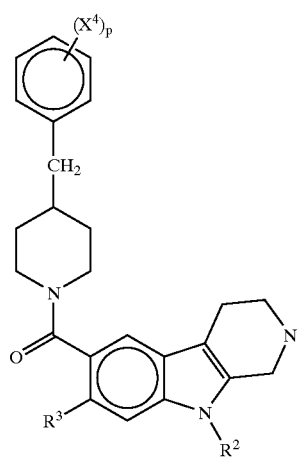
(B)

or having the structure of formula (A) or (B) wherein the positions on the benzo moiety of the tricyclic nucleus occupied by $R^3$ and the substituent

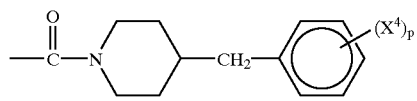

are reversed, wherein $R^2$ is H, or is alkyl (1–6C) or aryl, each of said alkyl or aryl optionally including one heteroatom which is O, S or N, and optionally substituted by one or more substituents selected from the group consisting of halo, CN, =O, OR, SR, $NR_2$, RCO, COOR, $CONR_2$, OOCR, and NROCR where R is H or alkyl (1–6C), and wherein when $R^2$ is alkyl said alkyl may be substituted by one or more substituents selected from the group consisting of piperazinyl, pyridinyl, piperidinyl and phenyl or wherein $R^2$ is —(CO) O $NR_2$ wherein n is an integer of 0–6 and R is H or alkyl (1–6C);

$R^3$ is H, halo, $NO_2$, alkyl (1–6C), alkenyl (1–6C), alkynyl (1–6C), CN, OR, SR, $NR_2$, RCO, COOR, $CONR_2$, OOCR, or NROCR where R is H alkyl (1–6C); and each $X^4$ is independently halo, alkyl (1–6C), OR, or $NR_2$, wherein R is H or alkyl (1–6C) and p is 0, 1, 2 or 3.

2. The compound of claim 1 wherein p is 0 or p is 1 or 2 and each $X^4$ is halo or OR where R is alkyl (1–3C).

3. The compound of claim 1 wherein $R^2$ is H.

4. The compound of claim 1 wherein $R^3$ is H, halo, or OR, wherein R is alkyl (1–6C).

5. The compound of claim 4 wherein $R^3$ is methoxy.

6. The compound of claim 3 where $R^3$ is H.

7. The compound of claim 1 wherein the position of the substituent

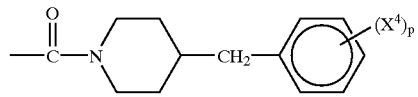

and the substituent illustrated as $R^3$ are reversed.

8. The compound of claim 1 wherein the substituents $R^3$ and

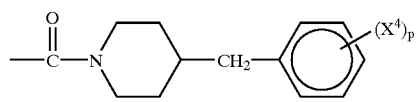

in formulas (A) and (B) are in the positions as shown.

9. The compound of claim 1 wherein $R^2$ is a polar group.

10. The compound of claim 1 wherein $R^2$ is —(CO) O—$(CH_2)_n$ $NR_2$ wherein in is 0–6 and R is H or alkyl (1–6C).

11. The compound of claim 1 which is

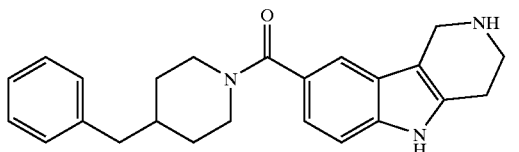

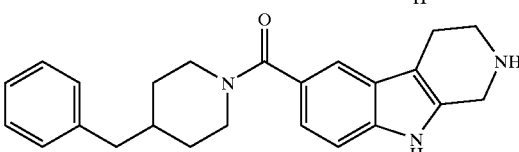

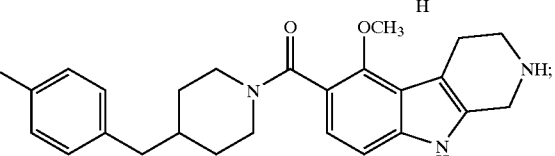

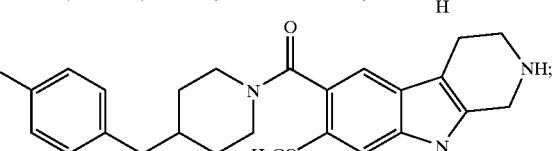

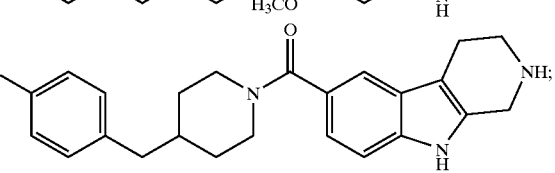

or

-continued

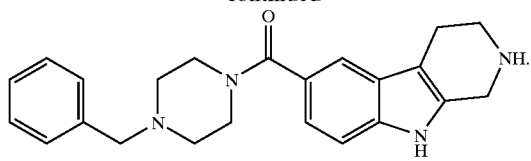

12. A pharmaceutical composition which comprises an effective amount of the compound of claim 1 along with at least one pharmaceutically acceptable excipient.

13. A method to treat a condition characterized by a proinflammation response which method comprises administering to a subject in need of such treatment an effective amount of the compound of claim 1 or a pharmaceutical composition thereof.

14. The method of claim 13 wherein said condition characterized by inflammation is acute respiratory distress syndrome, asthma, chronic obstructive pulmonary disease, uveitis, IBD, acute renal failure, head trauma, ischemic/reperfusion injury, osteoarthritis, rheumatoid arthritis or psoriasis.

15. A method to treat a heart condition associated with cardiac failure which method comprises administering to a subject in need of such treatment an effective amount of the compound of claim 1 or a pharmaceutical composition thereof.

16. The method of claim 15 wherein said heart condition is congestive heart failure, cardiomyopathy, restenosis, or myocarditis.

17. The method of claim 13 wherein said condition characterized by inflammation is vasculitis, atherosclerosis, rheumatoid spondylitis, gouty arthritis, multiple sclerosis, silicosis, pulmonary sarcosis, sepsis, septic shock, endotoxic shock, toxic shock syndrome, brain failure characterized by ischemia and reperfusion injury, CNS injuries, inflammatory eye conditions, glomerulonephritis, inflammatory bowel diseases, graft vs. host disease, bone resorption diseases, type II diabetes, pyresis, cachexia, viral diseases, cerebral malaria, tumor metastases, and acute pain or is caused from surgical procedures.

\* \* \* \* \*